United States Patent [19]

Flockerzi et al.

[11] Patent Number: 4,975,440

[45] Date of Patent: * Dec. 4, 1990

[54] OPTICALLY-ACTIVE 1,4-DIHYDROPYRIDINE

[75] Inventors: Dieter Flockerzi, Allensbach; Wolf-Rüdiger Ulrich, Constance, both of Fed. Rep. of Germany

[73] Assignee: Byk Gulden Lomberg Chemische Fabrik GmbH, Constance, Fed. Rep. of Germany

[ * ] Notice: The portion of the term of this patent subsequent to Nov. 17, 2004 has been disclaimed.

[21] Appl. No.: 31,834

[22] Filed: Mar. 27, 1987

Related U.S. Application Data

[63] Continuation-in-part of Ser. No. 781,808, Sep. 30, 1985, Pat. No. 4,707,486.

[30] Foreign Application Priority Data

| Sep. 28, 1984 | [CH] | Switzerland | 04653/84 |
| Sep. 28, 1984 | [CH] | Switzerland | 04652/84 |
| Mar. 27, 1986 | [CH] | Switzerland | 01263/86 |

[51] Int. Cl.$^5$ .................. A61K 31/445; C07D 211/14
[52] U.S. Cl. ...................................... 514/318; 546/194
[58] Field of Search ................ 546/321, 194; 514/318

[56] References Cited

U.S. PATENT DOCUMENTS

| 3,933,862 | 1/1976 | Williams et al. | |
| 4,021,434 | 5/1977 | Murakami et al. | 546/321 |
| 4,031,104 | 6/1977 | Bossert et al. | 540/321 |
| 4,102,905 | 7/1978 | Williams et al. | |
| 4,145,432 | 3/1979 | Sato | 546/321 |
| 4,158,060 | 6/1979 | Kaplan et al. | 546/230 |
| 4,179,461 | 12/1979 | Marhold et al. | 568/33 |
| 4,450,165 | 5/1984 | Araki et al. | 546/321 |
| 4,505,920 | 3/1985 | Loev et al. | 546/321 |
| 4,510,310 | 4/1985 | Wehinger et al. | 546/321 |
| 4,578,467 | 3/1986 | Bonacchi et al. | 514/252 |
| 4,707,486 | 11/1987 | Flockerzi et al. | 546/321 |

FOREIGN PATENT DOCUMENTS

| 117416 | 9/1984 | European Pat. Off. | |
| 1950394 | 4/1970 | Fed. Rep. of Germany. | |
| 1668029 | 7/1971 | Fed. Rep. of Germany. | |
| 2003112 | 7/1971 | Fed. Rep. of Germany. | |
| 84/02132 | 6/1984 | PCT Int'l Appl. | 546/321 |

OTHER PUBLICATIONS

Shibanuma et al., Chem. Pharm. Bull., 28(9), 2809–2812 (1980).
Poindexter et al., CA 106: 32841y.
Jaunin et al., CA, 105: 60534y.

*Primary Examiner*—Jane T. Fan
*Attorney, Agent, or Firm*—Berman, Aisenberg & Platt

[57] ABSTRACT

The invention relates to 3-methyl-5-[3-(4,4-diphenyl-piperid-1-yl)-propyl] (+)-1,4-dihydro-2,6-dimethyl-4-(3-nitrophenyl)-piperidine-3,5-dicarboxylate and its salts and to their preparation and use.

7 Claims, No Drawings

OPTICALLY-ACTIVE 1,4-DIHYDROPYRIDINE

RELATED APPLICATION

This application is a continuation-in-part of application Ser. No. 781,808, (now USP 4,707,486) filed Sept. 30, 1985. The entire disclosure of that parent application is incorporated herein by reference.

FIELD OF INVENTION

The invention relates to a new optically-active compound and to a process for its preparation. The new compound is employed in the pharmaceutical industry for the preparation of medicaments.

TECHNICAL BACKGROUND

Certain 1,4-dihydropyridine derivatives substituted in the 4-position have pharmacologically-useful properties. Such 1,4-dihydropyridine derivatives - insofar as they are substituted differently (unsymmetrically) in positions 2 and 6 and/or in positions 3 and 5 - have a chirality center in position 4. In addition the pharmacological properties of the 1,4-dihydropyridines are affected by the absolute configuration in the 4-position. The pure enantiomer of a chiral dihydropyridine (described in greater detail in the following description) has unexpectedly strong pharmacological activity by which it is distinguished in a surprising manner from the pure dihydropyridine enantiomers hitherto known.

SUMMARY OF THE INVENTION

The invention relates to the enantiomer of 3-methyl5-[3-(4,4-diphenylpiperid-1-yl)-propyl]1,4-dihydro-2,6-dimethyl-4-(3-nitrophenyl)-pyridine-3,5-dicarboxylate which rotates linearly polarized light of wavelength 589 nm in the (+)-direction, that is 3-methyl-5-[3-(4,4-diphenylpiperid-1-yl)-propyl](+)-1,4-dihydro-2,6-dimethyl-4-(3-nitrophenyl)-pyridine-3,5-dicarboxylate and its salts. The invention further relates to preparing and using the enantiomer and to compositions based on said enantiomer. All references to the enantiomer includes both the enantiomer and its salts in the absence of a contrary indication.

DETAILS

The compound according to the invention is described (without taking account of the absolute configuration in the 4-position of the 1,4-dihydropyridine) by formula (I):

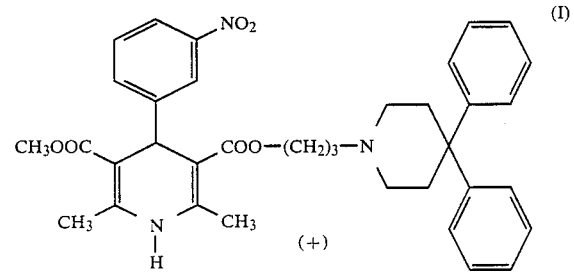

Suitable salts include all salts with acids, particularly the pharmacologically-acceptable salts of inorganic and organic acids customarily used in the pharmaceutical industry. Pharmacologically-unacceptable salts, which are, e.g., initially obtained as process products in preparing compounds according to the invention on an industrial scale are readily converted into pharmacologically-acceptable salts by conventional processes known to those skilled in the art. Examples of suitable salts of this type are water-soluble and water-insoluble acidaddition salts, such as the hydrochloride, hydrobromide, hydriodide, phosphate, nitrate, sulfate, acetate, citrate, gluconate, benzoate, hibenzate, fendizoate, butyrate, sulfosalicylate, maleate, laurate, malate, fumarate, succinate, oxalate, tartrate, amsonate, metembonate, stearate, tosylate, 2-hydroxy-3-naphthoate, 3-hydroxy-2-naphthoate or mesylate, and also salts with bumetanide, furosemide, azosemide, galosemide, besunide, piretanide, etacrynic acid, tienilinic acid or 4-chlorosulfamoylbenzoic acid.

A process for the preparation of compound (I) is characterized by reacting an N-protected dihydropyridinecarboxylic acid of formula II

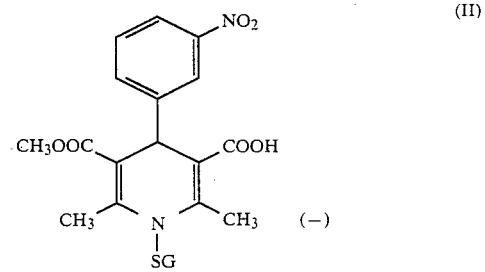

with 1,3-dibromopropane, and (after removal of the protecting group SG) reacting the resultant bromopropyl ester III

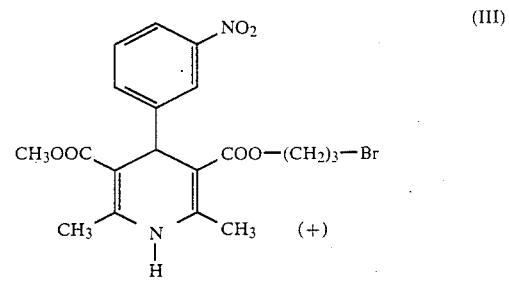

With diphenylpiperidine, or a salt thereof, to obtain the final product I. Any produced salt of compound I is optionally converted into the free base or a different salt; the free base is optionally converted into a salt. Such conversions are entirely conventional.

The reaction of II with dibromopropane is carried out under basic conditions in the presence of a phase-transfer catalyst.

Illustrative catalysts, besides onium salts, such as tetrabutylammonium bromide or benzyltriethylammonium chloride, are particularly crown ethers, such as dibenzo-[18]crown-6,dicyclohexyl-[18]crown-6 and, in particular, [18]crown-6.

A suitable base is employed in at least a molar amount and preferably in excess thereof. The base is, e.g., an inorganic base, such as an alkali-metal hydroxide (for example sodium hydroxide or potassium hydroxide) or, in particular, an alkali-metal carbonate (for example sodium carbonate or, preferably, potassium carbonate). When the reaction is carried out in an anhydrous solvent, the hydroxide or carbonate used is preferably in finely-powdered form.

The reaction is carried out (depending on the type of phase-transfer catalyst and the base employed) in water-containing or anhydrous organic solvent, or in a mixture of water and a water-immiscible or sparingly water-miscible organic solvent. Examples of water/solvent mixtures include mixtures of water with chloroform, dichloromethane or benzene. Examples of water-containing or anhydrous solvents are dichloromethane, acetonitrile or acetone.

The solvents, bases and phase-transfer catalysts in the examples only represent an exemplary selection. Which further combinations of solvents, bases and phase-transfer catalysts are also suitable is known to the expert on the basis of his expert knowledge.

The choice of reaction temperature in the reaction of II with dibromopropane depends on the other reaction conditions; temperatures between 20° C. and the boiling point of the solvent employed are generally preferred.

Suitable protecting groups SG are, in particular, those groups which are introduced easily and in high yield into the precursor on which the compound II is based, which do not undergo side reactions during the reaction of II with 1,3-dibromopropane, and which are removed smoothly at the end of the reaction. Examples of preferred protecting groups SG are alkoxymethyl groups or benzyloxymethyl groups, in particular the ethoxymethyl group. The removal of the protecting group is carried out in acidic medium, for example in 1 N hydrochloric acid or, preferably, in anhydrous formic acid, under reaction conditions which are known to the expert.

The reaction of the bromopropyl ester III with diphenylpiperidine is carried out in a fashion which is known to the expert for the reaction of alkyl halides with secondary amines.

The reaction is carried out in suitable, preferably inert, organic solvent in the presence of water or without water. Examples of such solvents are ethers, such as dioxane, diethyl ether, tetrahydrofuran, glycol monoethyl ether or glycol dimethyl ether; ketones, such as acetone or ethyl methyl ketone; aromatic hydrocarbons, such as xylene or toluene; or chlorinated hydrocarbons, such as methylene chloride, chloroform, tetrachloroethylene or dichloroethane.

Depending on the reactivity of the educts, the reaction temperatures are optionally varied within a wide range. In general, the reaction is carried out at temperatures between 20° C. and 150° C., preferably between 20° C. and 100° C., in particular at the boiling point of the solvent used.

The process is conveniently carried out at atmospheric pressure or at increased pressure, work at atmospheric pressure being the rule. The reaction is carried out in the presence of a base (for example an inorganic carbonate, such as potassium carbonate) or using an excess of diphenylpiperidine.

The resultant compound I (according to the invention) is isolated and purified in a fashion which is known per se, for example by removing the solvent by distillation in vacuo and recrystallizing the resultant residue from a suitable solvent, or by subjecting it to one of the conventional purification methods, such as column chromatography on a suitable support material.

Acid-addition salts are obtained by dissolving the free base in a suitable solvent, for example in a chlorinated hydrocarbon, such as methylene chloride or chloroform, or a low-molecular-weight aliphatic alcohol (ethanol or isopropanol), or a open-chain or cyclic ether, such as dioxane or tetrahydrofuran, which contains the desired acid or to which the desired acid is subsequently added.

The salts are obtained by filtration, reprecipitating, precipitating with a nonsolvent for the addition salt, or by evaporation of the solvent.

The salts obtained are converted into the free bases by alkalization, for example using aqueous ammonia solution; and the free bases are, in turn, converted into acid-addition salts. In this fashion, pharmacologically-unacceptable acid-addition salts are easily converted into pharmacologically-acceptable acid-addition salts.

Compounds of formula II are known from Chem. Pharm. Bull. 28(9) 2809–2811 (1980), or are prepared in an analogous fashion to that described therein.

A further process for the preparation of the compound according to the invention is characterized by reacting 3-methyl-5-[3-(4,4-diphenylpiperid-1-yl)-propyl](±)-1,4-dihydro-2,6-dimethyl-4-(3-nitrophenyl)-pyridine-3,5-dicarboxylate with a pure enantiomer of an optically-active acid. The resulting diastereoisomeric salts are separated, and 3-methyl-5-[3-(4,4-diphenylpiperid-1-yl)-propyl](+)-1,4-dihydro-2,6-dimethyl-4-(3-nitrophenyl)-pyridine-3,5-dicarboxylate is liberated from the desired diastereoisomeric salt by adding a base. The thusobtained free base is optionally converted into a salt.

Examples of useful optically-active acids are di-0,0'-p-toluoyltartaric acid or, in particular, di-0,0'-benzoyltartaric acid. A suitable separation process is preferably recrystallization.

The diastereoisomeric salts of uniform configuration which are separated by means of these methods are converted into the optically-active pure enantiomer of the compound according to the invention, preferably by adding inorganic base, such as ammonia, or by means of a basic ion exchanger.

The isolation and purification of the compound according to the invention is effected in a manner which is in itself known, for example by removing solvent by vacuum distillation and recrystallizing the resulting residue from a suitable solvent, or by subjecting it to a conventional method of purification, such as column chromatography over a suitable support.

Acid-addition salts are obtained by dissolving the free base in a suitable solvent, for example, in a chlorinated hydrocarbon, such as methylene chloride or chloroform, or a low-molecular aliphatic alcohol (ethanol or isopropanol), which contains the desired acid or to which the desired acid is subsequently added.

The salts are isolated by filtration, reprecipitation, precipitation with a non-solvent for the addition salt or by evaporating the solvent.

Resulting salts are converted into the free bases by rendering them alkaline, for example, with aqueous ammonia solution, and the free bases are, in turn, converted into acidaddition salts. Pharmacologically-unacceptable acid-addition salts are converted in this manner into pharmacologicallyacceptable acid-addition salts.

The preparation of the racemate on which the compound according to the invention is based, that is the preparation of the 1:1 mixture with the corresponding (−)-enantiomer, is described in the examples.

The following preparation examples are intended to illustrate the invention in greater detail, without limiting it. M.p. denotes melting point, h represents hours, b.p. represents boiling point, and decomp. denotes decomposition, M represents molarity, N represents normality and d represents density.

EXAMPLE I (+)-3-Methyl-5-[3-(4,4-diphenylpiperid-1-yl)-propyl]1,4-dihydro-2,6-dimethyl-4-(3-nitrophenyl)-pyridine-3,5-dicarboxylate hydrochloride A mixture of 13 g of (+)-3-methyl-5-(3-bromopropyl) 1,4-dihydro-2,6-dimethyl-4-(3-nitrophenyl)-pyridine-3,5-dicarboxylate, 7.85 g of 4,4-diphenylpiperidine hydrochloride and 12 g of potassium carbonate is refluxed for 14 h in 120 ml of toluene and 25 ml of water under a nitrogen atmosphere and with vigorous stirring. After cooling, the phases are separated; the organic phase is washed twice with water, dried over sodium sulfate and concentrated in vacuo. The oily residue is dissolved in 140 ml of dioxane; then 2.3 ml of concentrated hydrochloric acid solution (12.5 M, d=1.19) are added, and 20 to 25 ml of the solvent mixture are removed by distillation in vacuo. The product crystallizes spontaneously on standing at room temperature or after trituration, and is filtered off by suction after 16 h, washed with dioxane and diisopropyl ether, and dried at 80° C. in vacuo. 16 g of the title compound {m.p. 158° to 160° C. and [α]22/D= +14.4°(c=1, methanol)} are obtained.

EXAMPLE II (+)-3-Methyl-5-(3-bromopropyl) 1,4-dihydro-2,6-dimethyl-4-(3-nitrophenyl)-pyridine-3,5-dicarboxylate 36 g of (−)-1-ethoxymethyl-1,4-dihydro-5-methoxycarbonyl-2,6-dimethyl-4-(3-nitrophenyl)-pyridine-3-carboxylic acid/cinchonidine salt are dissolved in 250 ml of chloroform; 260 ml of 0.2 N hydrochloric acid solution are added, and the mixture is stirred vigorously. The pH is adjusted to 2 by adding 2 N hydrochloric acid solution, and the phases are then separated. The organic phase is washed a total of four times with pH 2 hydrochloric acid solution, and then washed with water, dried over sodium sulfate and concentrated. The obtained oily residue is dissolved in 200 ml of acetone. 16 g of finely powdered potassium carbonate, 80 ml of 1,3-dibromopropane and 0.5 g of [18]-crown-6 are subsequently added. The mixture is stirred vigorously for 16 h at room temperature and then filtered by suction; the filter cake is washed with acetone. The acetone is stripped off under a slight vacuum in a rotary evaporator, and the excess 1,3-dibromopropane is removed by distillation at 0.02 mbar. 160 ml of concentrated formic acid are poured onto the oily residue with ice cooling; the mixture is then stirred at room temperature until a clear solution has been produced (about 15 minutes). The formic acid is removed by distillation in vacuo. After twice adding and removing (by distillation) 50 ml of toluene in each case, the residue is dissolved in dichloromethane. The solution is stirred with sodium hydrogen carbonate solution (pH 8.5). The organic phase is dried over sodium sulfate and concentrated. The oily residue is then crystallized from cold methanol. 18.9 g of the title compound {m.p. 112° to 114° C. and [α]22/D= +13.8°(c=1, methanol)} are obtained.

EXAMPLE III (±)-1,4-dihydro-2,6-dimethyl-4-(3-nitrophenyl)-pyridine-3,5-dicarboxylic acid 3-methyl-5-[3-(4,4-diphenylpiperid-1-yl)-propyl] ester-hydrochloride 4.53 g of 3-nitrobenzaldehyde, 3.45 g of methyl 3-aminocrotonate and 11.38 g of 3-(4,4-diphenylpiperid-1-yl)propyl acetoacetate in 100 ml of 2-propanol are heated to the boil under reflux over night. The resulting solution is cooled and concentrated to dryness, and the residue which remains is chromatographed over a silica gel column using ethyl acetate as the mobile phase. After being concentrated, the single-substance fractions of product leave a solid, foamed residue, which is dissolved in methanol, and etheral hydrochloric acid is added. The obtained solution is concentrated, the solid residue which remains is taken up in a little methanol, and the title substance [m.p.: from 135° C. (decomposition); yield: 9.3 g] is precipitated by adding petroleum ether.

The free base of the title compound, which is required for the separation of enantiomers, is obtained by taking up foamed, solid residue (remaining after the condensation mixture has been concentrated) in a little methylene chloride; when diisopropyl ether is added until there is a permanent fine cloudiness, the base (m.p.: 145° to 147° C.) crystallizes out in fine platelets-oh standing in a refrigerator.

The starting compounds are obtained as follows: 3-(4,4-diphenylpiperid-1-yl)-propyl acetoacetate 23.6 g of 3-(4,4-diphenylpiperid-1-yl)-propanol are dissolved in 100 ml of absolute toluene, and 16 ml of a 50% strength solution of diketene in acetone are added with stirring. After standing for several days at room temperature (monitored by thin layer chromatography), the mixture is concentrated, and the residue is dried in a high vacuum. The pale yellow, viscous oil which remains is employed without further purification for the next stage.

(b) 3-(4,4-diphenylpiperid-1-yl)-propanol 40 g of 4,4-diphenylpiperidine, 24.7 g of 3-bromopropanol, 116.4 g of powdered potassium carbonate and approximately 1 g of potassium iodide (in 500 ml of a 1:1 mixture of dioxane and 1-butanol) are heated at the boil for about 48 hours under reflux and with vigorous stirring. After cooling, the mixture is filtered, and the filtrate is concentrated. The oily residue is taken up in ethyl acetate, and the solution is filtered again. Concentrating the filtrate to dryness gives the product in the form of a yellowish, oily residue which slowly solidifies to a wax-like product (yield: 44.8 g). Hydrochloric acid in ether produces the hydrochloride (m.p.: 226° to 227° C.), which is recrystallized in 2-propanol.

Alternatively, the starting compound (b) is obtained by heating 352 g of 4,4-diphenylpiperidine, 128 g of sodium hydroxide granules, 2.5 liters of methylene chloride, 500 ml of water, 218 g of 3-bromo-1-propanol and catalytic amounts of a phase-transfer catalyst (for example benzyltrimethylammonium chloride) at the boil under reflux for 10 hours. The organic phase is separated off and washed with water, and the combined water phases are extracted with methylene chloride. The combined organic phases are dried with sodium sulfate, and the resulting clear, brownish solution is evaporated to dryness. The resinous, brown residue is taken up in 4.5 liters of boiling petroleum ether (boiling range 100° to 140° C.); the solution is filtered while hot to remove the insoluble residue and is then cooled. Allowing the product to stand overnight yields the starting compound in the form of the free base in colorless, coarse crystals (m.p.: 97° C.; yield: 303 g).

EXAMPLE IV (+)-1,4-dihydro-2,6-dimethyl-4-(3-nitrophenyl)-pyridine-3,5-dicarboxylic acid 3-methyl-5-[3-(4,4-diphenylpiperid-1-yl)-propyl]-ester-(+)-di-0.0'-benzoyltartrate 18.2 g of 3-methyl-5-[3-(4,4-diphenylpiperid-1-yl)propyl (±)-1,4-dihydro-2,6-dimethyl-4-(3-nitrophenyl)-3,5-dicarboxylate and 11.29 g of commercial D-(+)-di-0,0'-benzoyltartaric acid hydrate {in the present example having a specific rotation $[\alpha]23/D$ of $+106°$ (c=5, ethanol)} are together dissolved in 100 ml of methanol. The clear solution is then concentrated to dryness, and the resulting crystalline residue is recrystallized at the boil in a mixture of 280 ml of chloroform and 20 ml of methanol. Allowing the solution to cool slowly gives a first crop of crystals of m.p.: 143° to 144° C.; yield: approximately 14 g {course, slightly yellowish needles, $[\alpha]23/D = +4°$ (c=5, ethanol)}. Further recrystallization of the first crop of crystals in chloroform/methanol gives a second crop of crystals of m.p.: 145° to 146° C.; yield: approximately 12 g {course, slightly yellowish needles, $[\alpha]23/D = +49°$ (c=5, ethanol)}. Further recrystallization of the second crop of crystals in chloroform/methanol gives a third crop of crystals of m.p. 147° to 148° C.; yield: approximately 9 g {course, slightly yellowish needles, $[\alpha]23/D = +50°$ (c=5, ethanol)}.

If D-(+)-di-0,0'-benzoyltartaric acid having a higher optical purity is used, the values of specific rotation of the resulting salts increase correspondingly.

EXAMPLE V (+)-1,4-dihydro-2,6-dimethyl-4-(3-nitrophenyl)-pyridine-3,5-dicarboxylic acid 3-methyl-5-[3-(4,4-diphenylpiperid-1-yl)-propyl] ester-hydrochloride 4.84 g of the third crop of crystals from Example IV are dissolved in 100 ml of methylene chloride and are extracted with three times 50 ml of half-concentrated aqueous ammonia solution. Each of the aqueous phases is again extracted with 50 ml of methylene chloride, and the combined organic phases are washed twice with 100 ml of water and are then dried over sodium sulfate. The methylene chloride solution is concentrated to dryness, and the resulting solid residue is dissolved in about 5 ml of methanol. Etheral hydrochloric acid is added to the resulting solution. The solution is again concentrated to dryness and the resulting solid residue is dissolved in 9 ml of hot dioxane. After the solution has cooled, the title compound is obtained in the form of fine clusters of needles {m.p.: from 142° to 162° C. (slow deliquescence); yield: 3.1 g; $[\alpha]22/D = +13.9°$ (c=1, methanol)}.

If D-(+)-di-0,0'-benzoyltartaric acid having a higher optical purity is used, the value of the specific rotation of the title compound increases correspondingly.

COMMERCIAL APPLICABILITY

The compound according to the invention and its salts possess valuable properties which make them commercially useful. They are, in particular, effective vasodilators having coronary therapeutic properties. The pharmacological activity of the compound according to the invention manifests itself in particular in a slowly-starting, powerful and long-lasting lowering of blood pressure. In addition, the compound according to the invention has an inhibiting action on the inflow of calcium and a promoting action on the outflow of potassium from cells (properties which relax smooth muscles) and peripheral, coronary, cerebral and renal vasodilator properties as well as salidiuretic, antithrombotic, antiarteriosclerotic and advantageous haemorheological properties.

In its excellent effectiveness, which is combined with low toxicity and the absence of appreciable side-effects, the compound according to the invention differs in a surprising and advantageous manner from compounds of the state of the art. The compound according to the invention differs in a surprising manner from its corresponding racemate, the (±)-1,4-dihydro-2,6-dimethyl-4-(3-nitrophenyl) pyridine-3,5-dicarboxylic acid 3-methyl-5-[3-(4,4-diphenylpiperid-1-yl)propyl] ester and from the corresponding (−)-enantiomer.

The following are examples of advantageous properties of the compound according to the invention: the extent of blood-pressure lowering, the long duration of bloodpressure lowering, the good controllability of bloodpressure lowering, the surprisingly low increase in heart rate (which disappears when the dose is repeated), the excellent bioavailability, the wide therapeutic range, the absence of central side-effects, the absence of kinetic interactions with other substances, the absence of development of tolerance, the balanced physical properties and the great stability.

The excellent effectiveness of the compound (according to the invention) and of its salts permits them to be used in human medicine, suitable indications being, in particular, primary (essential) and secondary, arterial and pulmonary hypertension of all degrees of severity, coronary cardiac disease (coronary insufficiency, angina pectoris, myocardial infarction, etc.), peripheral and cerebral circulatory disturbances (apoplexy, temporary cerebral circulatory disturbances, migraines, vertigo, renal narrowing of arteries, etc.), hypertrophic cardiomyopathy, cardiac insufficiency, diseases due to an increased retention of water and sodium and diseases due to an increased inflow of calcium, such as spasms of organs having smooth muscles (respiratory passages, gastrointestinal tract, urogenital tract, etc.) and also arrhythmia, arteriosclerosis and cell damage of different geneses (e.g. hypoxia).

The invention therefore also relates to a process for prophylaxis and for treating mammals, in particular humans, subject to or suffering from one of the noted conditions or diseases. The process is characterized by administering a therapeutically-effective and pharmacologically-acceptable amount of the compound according to the invention (or of a pharmacologically-acceptable salt thereof) to a patient in need of such treatment.

The invention relates additionally to the compound according to the invention and its pharmacologically-acceptable salts for use in the treatment of said diseases.

The invention also embraces the use of the compound according to the invention and its pharmacologically-acceptable salts in the preparation of medicaments which are employed for combating said diseases.

The invention also relates to medicaments containing the compound according to the invention and/or its pharmacologically-acceptable salts.

The medicaments are prepared by processes which are in themselves known and are familiar to those skilled in the art. The medicaments employed are the pharmacologically-active compound according to the invention and/or its pharmacologicallyacceptable salts (=active compounds), either as such or, preferably, in combination with suitable pharmaceutical auxiliaries, in the form of tablets, coated tablets, capules, suppositories, plasters (for example as TTS), emulsions, suspensions, aerosols, sprays, ointments, creams, gels or solutions, the content of active compound (of this invention being advantageously between 0.1 and 95 per cent by weight.

Those skilled in the art are familiar, by virtue of their specialized knowledge, with the auxiliaries which are suitable for the desired formulations of medicaments. In addition to solvents, gel-formers, suppository bases, tablet auxiliaries and other excipients for active compounds, the following are optionally employed: antioxidants, dispersing agents, emulsifiers, anti-foaming agents, taste correctives, preservatives, solubilizers, colorants or, in particular, permeation promoters and complex-formers (for example cyclodextrins).

The active compounds are administered orally, rectally, by inhalation or parenterally (in particular perlingually, intravenously or percutaneously).

In general, it is advantageous in human medicine to administer the active compound or active compounds, when these are given orally, in a daily dose of from about 0.01 to about 10, preferably 0.05 to 5, mg/kg of body weight, if desired in the form of several, preferably 1 to 4, individual administrations in order to achieve the desired results. In the case of parenteral treatment similar dosages or (particularly when the active compounds are administered intravenously) generally lower dosages are used. In the case of therapy with a low initial dosage, a fairly small dose is administered at the start of the treatment, and a change to a higher dose is then carried out slowly. After the desired result of the therapy has been achieved, a return is made to a smaller dose.

The optimum dosage and mode of administration of the active compounds required in a particular case can readily be determined by anyone skilled in the art, by virtue of his expert knowledge.

When a compound according to the invention and/or its pharmacologically-acceptable salt is employed for the treatment of indicated diseases, the pharmaceutical formulations optionally contain one or more other pharmacologically-active constituents of other groups of medicaments, such as other vasodilators, antihypertensive agents, alpha-1-receptor blockers, alpha-2-receptor stimulators, beta-1-receptor blockers, beta-2-receptor stimulators, ACE-inhibitors, nitro compounds, cardiotonic agents, diuretics, saluretics, alkaloids, analgesics, lipid-lowerers, anticoagulants, anticholinergic agents, methylxanthines, antiarrhythmics, antihistamines, dopamine stimulators, serotonin receptor blockers, etc., such as nifedipine, dihydralazine, prazosin, clonidine, atenolol, labetalol, fenoterol, captopril, isosorbide dinitrate, digoxin, milrinon, mefruside, clopamide, spironolactone, chlorthalidone, furosemide, polythiazide, hydrochlorothiazide, reserpine, dihydroergocristine, rescinnamine, rauwolfia combined alkaloids, acetylsalicylic acid, bezafibrate, warfarin, atropine, theophylline, lidocaine, astemizol, bromocryptine, ketanserine, etc.

PHARMACOLOGY

The antihypertensive activity of the compound according to the invention is demonstrated with spontaneously hypertonic rats as a model.

In order to determine the antihypertensive action, the compound is administered under acute conditions in the doses indicated to groups of 6 or 12 conscious rats (strain SHR/N/Ibm/Bm ♂,350–400 g) having genetically induced hypertension (arterial mean pressure 160 to 200 mm Hg), administration being carried out intravenously by injection via a catheter into the Vena jugularis or intragastrically by means of a probang. The blood pressure is measured continuously up to 6 hours after the administration of the substance via a catheter placed in the Aorta abdominalis and a conventional pressure recorder using a piezo-electric pressure converter. Values of blood pressure are taken within a narrow time-slot pattern up to 60 minutes after the administration of the substance (1, 3, 5, 10, 15, 30, 45 and 60 minutes after intravenous administration and 5, 10, 20, 30, 40, 50 and 60 minutes after peroral administration) and subsequently at hourly intervals up to 360 minutes after the administration of the substance. The AUC (area under the curve) is then determined as a measure of the change in blood pressure caused by the administration of the substance, this determination being carried out a) for the fractional time period of 0 to 60 minutes and b) for 60 to 360 minutes after.

Tables I and II show the average lowering in blood pressure (mm Hg) for the compound according to the invention (=compound No.1), for the corresponding racemate (=compound No. 2) and for the corresponding (−)-enantiomer (=compound No. 3) in the two fractional time periods mentioned after intravenous administration of the substances (Table I) and after peroral administration of the substances (Table II).

TABLE I

Average lowering of the blood pressure of genetically hypertonic rats (n = number) after acute intravenous administration:

| Compound No. | Dose, μmol/kg | n | AUC (mmHg) 0–60 min. | 60–360 min. |
|---|---|---|---|---|
| 1 | 0.03 | 6 | −33 | −14 |
| 1 | 0.1 | 12 | −70 | −39 |
| 2 | 0.03 | 6 | −12 | +1 |
| 2 | 0.1 | 6 | −58 | −25 |
| 3 | 1.0 | 6 | −10 | +4 |
| 3 | 3.0 | 6 | −30 | +1 |

TABLE II

Average lowering of the blood pressure of genetically hypertonic rats (n = number) after acute peroral administration: (in solution):

| Compound No. | Dose, μmol/kg | n | AUC (mmHg) 0–60 min. | 60–360 min. |
|---|---|---|---|---|
| 1 | 1 | 12 | −16 | −34 |
| 1 | 3 | 6 | −44 | −79 |
| 2 | 1 | 6 | −7 | −31 |
| 2 | 3 | 6 | −27 | −47 |
| 3 | 10 | 6 | −12 | −6 |
| 3 | 30 | 6 | −4 | −19 |

What is claimed is:

1. A compound which is 3-methyl-5-[3-(4,4-diphenyl-piperid-1-yl)-propyl](+)-1,4-dihydro-2,6-dimethyl-4-(3-nitrophenyl)-pyridine-3,5-dicarboxylate or a salt thereof.

2. The compound of claim 1 which is (+)-1,4-dihydro-2,6-dimethyl-4,(3-nitrophenyl)-pyridine-3,5-dicarboxylic acid 3-methyl-5-[3-(4,4-diphenylpiperid-1-yl)-propyl] ester-hydrochloride.

3. A medicament composition containing from 0.1 to 95 per cent by weight of a pharmacologically-acceptable compound of claim 1 suitable excipient.

4. A compound according to claim 1 which is pharmacologically acceptable.

5. A pharmacologically-acceptable salt of claim 4.

6. A process for the treatment of hypertension, of coronary cardiac diseases, of peripheral and cerebral circulatory disturbances and of diseases due to an increased retention of water or sodium, which comprises administering an effective amount of compound of claim 4 to a patient afflicted with at least one such condition.

7. A process for the prophylaxis of hypertension, of coronary cardiac diseases, of peripheral and cerebral circulatory disturbances and of diseases due to an increased retention of water or sodium, which comprises administering an effective amount of compound of claim 4 to a patient subject to at least one such condition.

* * * * *